(12) United States Patent
Dela

(10) Patent No.: US 9,867,688 B2
(45) Date of Patent: Jan. 16, 2018

(54) HAIR PIN IVC FILTER

(71) Applicant: Cook Medical Technologies, LLC, Bloomington, IN (US)

(72) Inventor: Christian Dela, Valby (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 306 days.

(21) Appl. No.: 14/863,564

(22) Filed: Sep. 24, 2015

(65) Prior Publication Data

US 2016/0120633 A1 May 5, 2016

Related U.S. Application Data

(60) Provisional application No. 62/072,731, filed on Oct. 30, 2014.

(51) Int. Cl.
*A61F 2/01* (2006.01)

(52) U.S. Cl.
CPC .......... *A61F 2/01* (2013.01); *A61F 2002/011* (2013.01); *A61F 2002/016* (2013.01); *A61F 2230/005* (2013.01); *A61F 2230/008* (2013.01)

(58) Field of Classification Search
CPC .... A61F 2/01; A61F 2/06; A61F 2/013; A61F 2002/011; A61F 2002/015; A61F 2002/016; A61F 2002/018; A61F 2002/061; A61F 2230/008; A61F 2230/005

See application file for complete search history.

(56) References Cited

U.S. PATENT DOCUMENTS

| 6,080,178 A | 6/2000 | Meglin |
| 6,436,120 B1 | 8/2002 | Meglin |

*Primary Examiner* — Jocelin Tanner
(74) *Attorney, Agent, or Firm* — Brinks Gilson & Lione

(57) ABSTRACT

The disclosure provides a hair pin IVC filter device and a method to retrieve said device from the vena cava. The device comprises a tubular backbone slidably disposed relative to a hub with a bore formed therethrough. A plurality of filter legs are each attached to the hub. Each filter leg has a first arcuate segment extending arcuately to a second arcuate segment. The first and second arcuate segments provide flexibility to the device when implanted for filtering in the vena cava. Upon retrieval, each filter leg may be converted from a hair pin position to a substantially straight position to remove the filter device from any endothelialized tissue.

20 Claims, 7 Drawing Sheets

HAIR PIN IVC FILTER

RELATED APPLICATIONS

This application claims the benefit of priority under 35 U.S.C. §119(a) to U.S. Provisional Application No. 62/072,731, filed on Oct. 30, 2014, which is incorporated by referenced here in its entirety.

BACKGROUND

1. Technical Field

The present disclosure relates to medical devices. More particularly, the disclosure relates to a hair pin IVC filter device and method to retrieve said device from a body vessel.

2. Background Information

Physicians may place filter devices within the vasculature to treat conditions such as pulmonary embolism and thrombosis. In particular, these devices may be placed in the vena cava. The vena cava is the largest vein in the body. It returns deoxygenated blood to the heart. The vena cava is flexible, and moves as the diaphragm expands and contracts during breathing. The vena cava may also move with a heartbeat. Filters in the vena cava may be placed using minimally invasive techniques either from the jugular or femoral vein. Such devices may contain close loop portions.

In some cases, looped filters exert a lower force on the vena cava wall, which may be desirable. However, said loops may become endothelialized within the body vessel tissue where the loops contact the vessel wall. If temporary placement is intended, such endothelization may make it difficult for the physician to remove these devices. There is a need for a loop filter device that is more easily retrieved. There is also a need for a loop filter device that may accommodate the flexible nature of the vena cava.

BRIEF SUMMARY

The present disclosure provides generally for a hair pin filter device. The device may include a hub having a body with a bore formed therethrough defining a first opening and a second opening. The device may further include a tubular backbone having a proximal end extending to a distal end along the longitudinal axis and a lumen formed therethrough. The tubular backbone may be slidably disposed through the hub between the proximal and distal ends. In addition, the device may include a plurality of filter legs, each filter leg having a first portion having a first end attached to the body and extending distally to a contact portion, the contact portion extending to a second portion having a second end removably disposed in the lumen adjacent to the distal end.

The second portion may have a first arcuate segment connected to the contact portion and extending arcuately to a second arcuate segment, the second arcuate segment extending arcuately to the second end. In one embodiment, one of the first and second arcuate segments extends substantially along a radial direction and the other of the first and second arcuate segments extends substantially along the longitudinal axis. The first arcuate segment extends substantially along the radial direction to the second arcuate segment extending substantially along the longitudinal axis.

Similarly, one of the first and second arcuate segments may have a semicircle. The first arcuate segment may have a first semicircle having a first semicircle end extending from the contact portion to a second semicircle end, the second arcuate segment may arcuately extend from the second semicircle end to the second end proximal the second semicircle end.

The plurality of filter legs may be four filter legs, each first end disposed circumferentially around the body about 90 degrees from the adjacent first end. Each filter leg may include a wire. The wire may include Nitinol or Elgiloy. The device may further include a plurality of secondary filter struts, each secondary filter strut having a proximal strut end attached to the body and extending distally to a distal strut end. Each distal strut end may be distal to the distal end and proximal the first arcuate segment.

The plurality of secondary filter struts may be four secondary filter struts, each proximal strut end being disposed circumferentially around the body about 45 degrees from the adjacent first end. Alternatively, the plurality of secondary filter struts may be eight secondary filter struts, with each proximal strut end being disposed circumferentially around the body about 30 degrees from the adjacent first end and the adjacent proximal strut end. Each secondary filter strut may be a wire. The wire may also include Nitinol or Elgiloy.

In addition, the tubular backbone may include a hook attached to the distal end for delivery and retrieval. The tubular backbone may also have a stop at the distal end. Each contact portion may be adapted for contacting the vessel wall. The device may further be part of a filter apparatus having an inner sheath and a coupling member wherein the device may be removably coupled to the inner sheath by way of the coupling member.

As one advantage, the device having first and second arcuate segments provides flexibility to accommodate the natural vena cave movement. This may minimizes any fatiguing of the device.

As an additional advantage, the device may be easily removed from possible endothelialization by converting the hair pin or loop into a substantially straight position for removal. In this position, the filter legs may move through the endothelialized tissue, reducing or eliminating any possible negative effects on the vessel wall. Preferably, no portion of the device remains in the body vessel after retrieval.

The disclosure also provides generally for a method for filtering with the disclosed device in the body vessel. The method may include (1) disposing the device within the body vessel; (2) applying a force in a proximal direction to the proximal end in the body vessel; (3) moving the tubular backbone proximally relative to the hub through the first and second openings; (4) moving the second end out of the lumen; (5) slidably removing each filter leg from the vessel wall; (6) and retrieving the device from the body vessel.

The step of disposing the device may include centering the device in the body vessel with the first and second arcuate segments. The step of moving the tubular backbone may include sliding the body along or relative to the tubular backbone between the proximal end and a stop at the distal end. The step of slidably removing each filter leg may include straightening each filter leg to remove each filter leg from the vessel wall. The step of straightening each filter leg may include straightening each filter leg to a substantially straight position.

DETAILED DESCRIPTION

The present disclosure provides a hair pin filter device and apparatus for filtering in the body vessel. The disclosure also provides a method of retrieving the device from the body vessel. Preferred methods, devices, and materials are described throughout. The methods, materials, and examples disclosed herein are illustrative only and not intended to be limiting. The disclosed figures are not necessarily drawn to scale.

All publications, patent applications, patents, and other references mentioned herein are incorporated by a reference in their entirety. Unless otherwise defined all scientific and technical terms used herein have the same meaning as commonly understood by one of ordinary skill in the art to which said disclosure pertains. In the case of conflict, the present document and definitions will control.

"About" or "substantially" used to refer to a given quantity means within 10%, preferably within 5%, more preferably within 1%. "Substantially" or derivatives thereof may also mean significantly or in large part when not used to refer to a given quantity.

"Adjacent" and derivatives thereof will be understood to mean nearby, near to, or in close proximity with.

"Longitudinally" and derivatives thereof will be understood to mean along the longitudinal axis of the body vessel.

The terms "proximal" and "distal" and derivatives thereof will be understood in the frame of reference of a medical physician using the medical device: thus proximal refers to locations closer to the physician and distal refers to locations farther away from the physician (e.g., deeper in the patient's vasculature).

"Radially" and derivatives thereof will be understood to mean along the radial axis of the body vessel.

Figure 1:
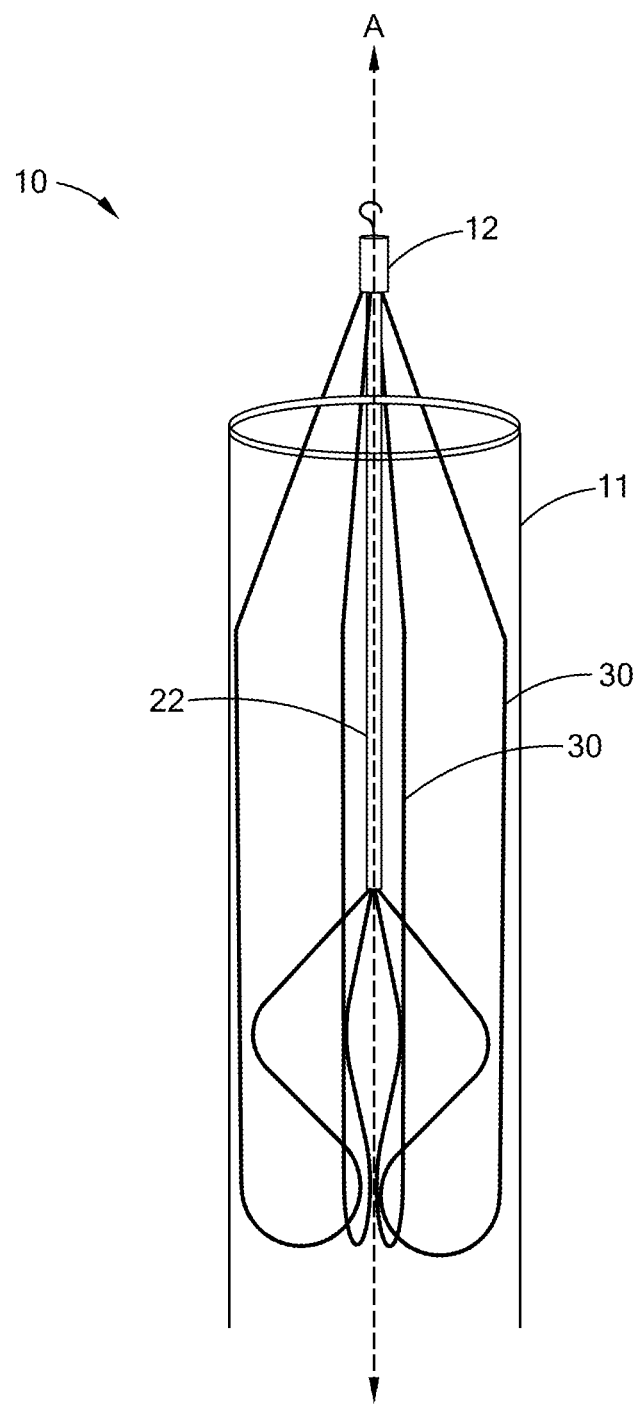
FIG. 1 is an environmental side view of the device for filtering in the body vessel in accordance with one embodiment of the present invention.

FIG. 1 illustrates the device 10 within the body vessel. The body vessel has a vessel wall 11 and a longitudinal axis A. The device 10 may comprise a hub 12, a tubular backbone 22, and a plurality of filter legs 30 spaced equally around the hub 12.

Each filter leg may generally or loosely resemble or have qualities attributable to a hair pin. Such qualities include a springy or a spring-like nature. Due to the loops and curves of a hair pin, it can work like a spring under a load without deforming. In the vena cava, a filter may need to accommodate movement due to heartbeat, diaphragm, or other natural movements when in the body vessel. These filter legs may move with the vena cava while avoiding deforming or tilting out of place.

Figure 2:
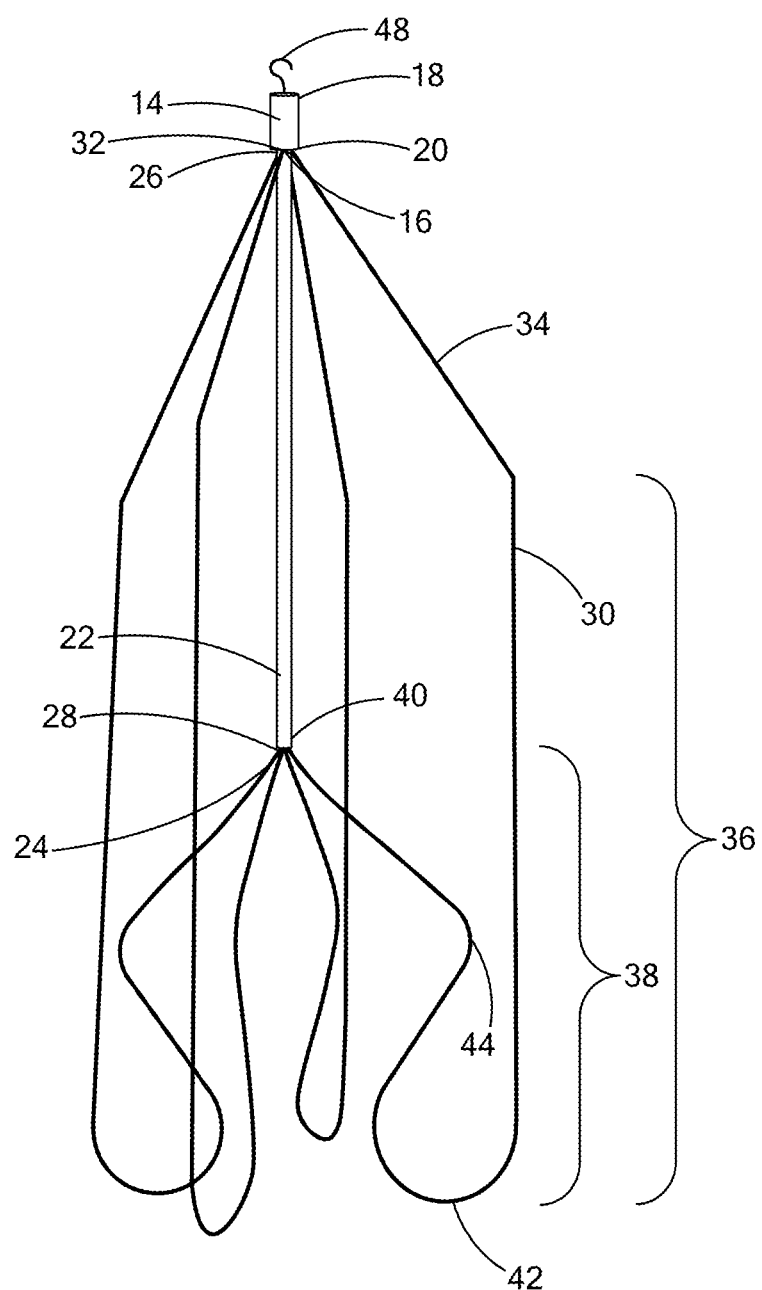
FIG. 2 is side view of one embodiment of the device of FIG. 1.

FIG. 2 provides a more detailed view of the device of FIG. 1. The device has a hub including a body 14 with a bore 16 formed therethrough, defining a first opening 18 and a second opening 20. The device further comprises a tubular backbone 22 having a proximal end 26 extending to a distal end 28 along the longitudinal axis and a lumen 24 formed therethrough. The tubular backbone 22 may be slidably disposed through or relative to the hub between the proximal and distal ends (26, 28, respectively).

Because of the small space inside bore 16 and the fit between bore 16 and the tubular backbone 22, it may be preferred to coat bore 16 and backbone 22 with an anticoagulation agent. Such agent may prevent coagulation, and allow movement between bore 16 and tubular backbone 22 while in the body vessel. One skilled in the art will understand that any such agent may prevent coagulation in these spaces, and the agent may be employed through any method known in the art. For example, a polymer coating may be deposited by chemical vapor deposition ("CVD") on the device.

The filter device comprises a plurality of filter legs 30. Each filter leg 30 may comprise a first portion 34 having a first end 32 attached to the body 14 and extending distally to a contact portion 36. The contact portion 36 may extend to a second portion 38 having a second end 40. The second end 40 may be removably disposed in the lumen 24 adjacent to the distal end 28. The second portion 38 may have a first arcuate segment 42 connected to the contact portion 36 and extending arcuately to a second arcuate segment 44. The second arcuate segment 44 may extend arcuately to the second end 40.

The first portion 34 of each filter leg may be attached to the body 14 through any method known in the art including gluing, soldering, welding, or clamping. In a preferred embodiment, the first portion 34 is fed through a hole in the body 14 and clamped inside the bore 16 to secure each filter leg 30 to the body 14.

The second portion 38 of each filter leg 30 comprises first and second arcuate segments. In one embodiment, one of the first and second arcuate segments (42, 44, respectively) extends radially (i.e. substantially along a radial direction) and the other of the first and second arcuate segments (42, 44, respectively) extends longitudinally (i.e. substantially along the longitudinal axis). Preferably, the first arcuate segment 42 extends radially to the second arcuate segment 44. The second arcuate segment may extend longitudinally. In this embodiment, the first and second arcuate segments extend along the radial and longitudinal axis of the body vessel, respectively. These arcuate segments provide a spring-like ability of each filter leg 30 to accommodate the vena cava movement.

Similarly, one of the first and second arcuate segments may have a semicircle. For example, the first arcuate segment may have a first semicircle (shown generally at 42) having a first semicircle end extending from the contact portion 36 to a second semicircle end. The second arcuate segment arcuately extends from the second semicircle end to the second end 40 proximal the second semicircle end. The second arcuate segment may also comprise a second semicircle (shown generally at 44).

One skilled in the art will understand that each filter leg may comprise any material known in the art for filtering in the body vessel. Preferably, each filter leg comprises a wire. More preferably, each wire comprises Nitinol or Elgiloy. Nitinol is a metal alloy of nickel and titanium having unique shape memory setting properties and being biocompatible. At a transition temperature, Nitinol may undergo a phase change from Martensite to Austenite, changing its structure. In addition to this phase change ability, Nitinol is also quite flexible.

Similarly, Elgiloy is a metal or super-alloy, also exhibiting flexibility. Elgiloy is slightly more flexible than traditional steel. A skilled artisan will understand that a similarly flexible material or metal may be used in the filter legs.

In a preferred embodiment, contact portion 36 is adapted for contacting the vessel wall. The contact portion, when disposed in contact with the vessel wall, may become ingrown. A skilled artisan will understand that the vessel wall tissue may naturally endothelialize the contact portion 36. Once endothelialization occurs, usually after two to three months' time, it may be difficult for the physician to remove the device. However, the device may be intended for temporary placement. In this case, the physician may employ a retrieval method to convert each filter leg to a substantially straight position for retrieval. This method is discussed below in further detail.

The tubular backbone 22 may comprise a hook 48 attached to the proximal end 26 for delivery and retrieval. In addition, the tubular backbone 22 may comprise a stop at the distal end 28. Such stop will prevent the body 14 from moving past the distal end 28. Once the device is expanded in the body vessel, the diameter of the device may be about 30 millimeters. In another embodiment, the diameter of the device in the expanded state may be about 18 millimeters. A skilled artisan will understand that the device may have an appropriate diameter for the intended body vessel. In addition, the length of the filter device from hook to the first arcuate segment may be about 50 millimeters.

Figure 3A:
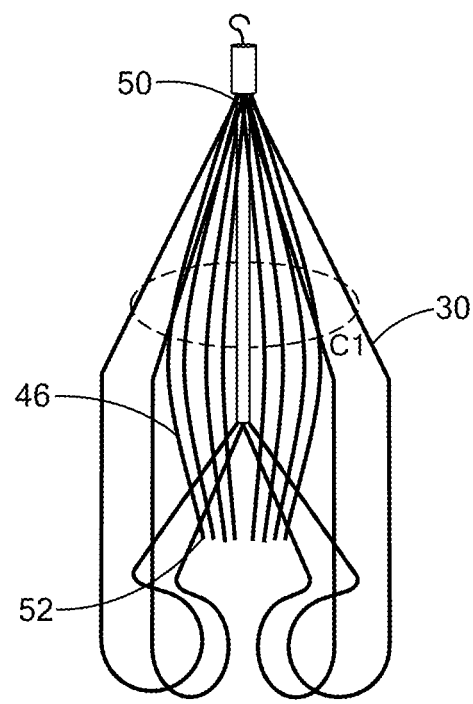
FIG. 3A is a side view of one embodiment of the device of FIG. 1.

FIG. 3A illustrates a second embodiment of the device. In this embodiment, the device may further comprise a plurality of secondary filter struts 46. Each secondary filter strut 46 may have a proximal strut end 50 attached to the body and extend distally to a distal strut end 52. In one embodiment, the distal strut end 52 may be distal to the distal end of the backbone. These secondary filter struts may provide additional stability for the filter device in the body vessel. In addition, the secondary filter struts may provide additional filtering capacity in the body vessel.

The number of secondary filter struts 46 may vary as necessary for the application. In one embodiment, a plurality of secondary filter struts 46 is four secondary filter struts 46. Each proximal end 50 may be disposed circumferentially around the body 14 about 45 degrees from the adjacent first end of the filter legs 30.

In another embodiment, the plurality of secondary filter struts 46 may be eight secondary filter struts 46. Each proximal strut end 50 may be disposed circumferentially around the body 14 about 30 degrees from both the adjacent first end and the adjacent proximal strut end 50. A skilled artisan will understand that increasing the number of filter struts may increase the filtering capacity and stability of the device.

Figure 3B:
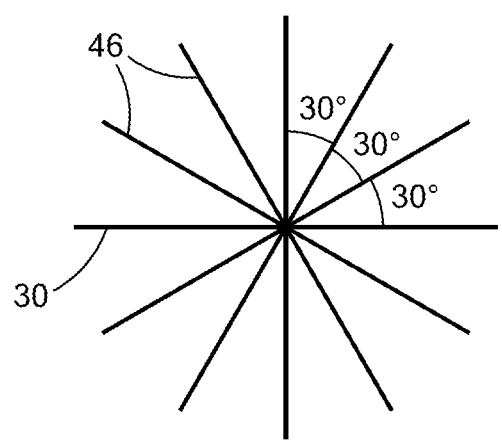
FIG. 3B is a cross sectional view of one embodiment of the device of FIG. 3A around cross section $C_1$.

FIG. 3B shows a cross sectional view of the device with eight secondary filter struts 46, from cross section $C_1$ in FIG. 3A. In this embodiment, each secondary filter strut is disposed 30 degrees from the adjacent first end of the filter leg 30 and the adjacent proximal strut end of the secondary filter strut 46.

A skilled artisan will understand that the material of the secondary filter struts may be any material known in the art appropriate for filtering in the body vessel. In a preferred embodiment, each secondary filter strut comprises a wire. More preferably, each wire comprises Nitinol or Elgiloy.

Figure 4A:
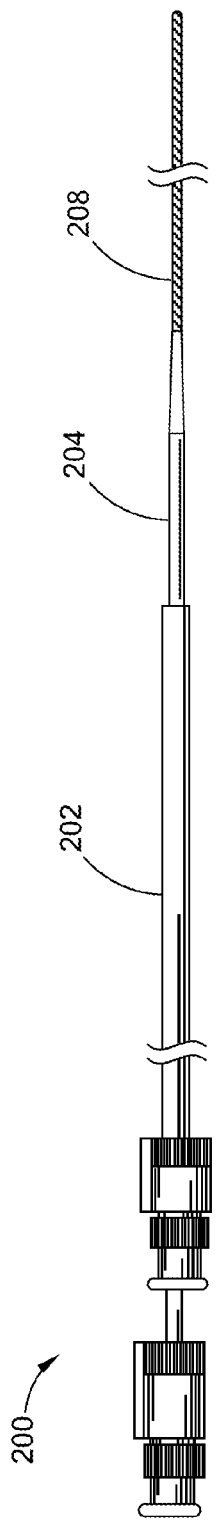
FIGS. 4A-4B depict a delivery assembly for introducing the device of FIG. 1.
Figure 4B:
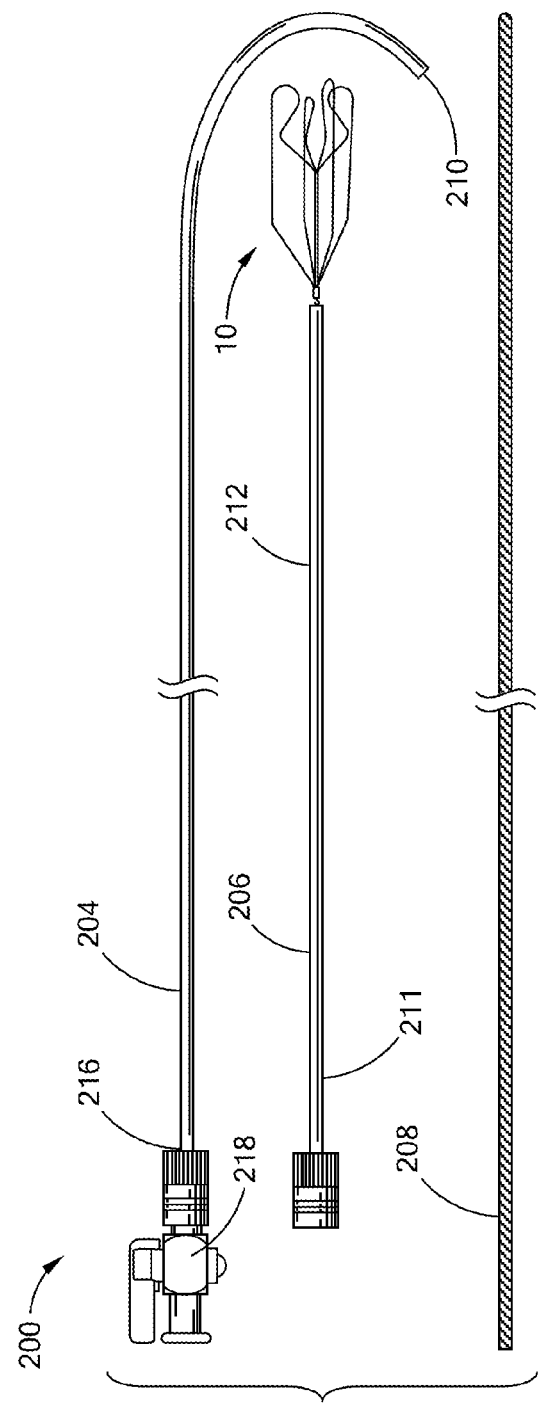

FIGS. 4A-4B depict a delivery or retrieval assembly for the device 10. The device 10 may be delivered or retrieved by way of the Seldinger technique. As shown, the delivery assembly 200 includes a polytetrafluoroethylene (PTFE) introducer sheath 202 for percutaneously introducing an outer sheath 204 into a body vessel. Of course, any other suitable material for the introducer sheath 202 may be used without falling beyond the scope or spirit of the present invention.

The introducer sheath 202 may have any suitable size, for example, between about 3-FR to 8-FR. The introducer sheath 202 serves to allow the outer sheath 204 and an inner sheath or catheter 206 to be percutaneously inserted to a desired location in the body vessel. The inner sheath may also include, for example, a stylet. The introducer sheath 202 receives the outer sheath 204 and provides stability to the outer sheath 204 at a desired location of the body vessel. For example, the introducer sheath 202 is held stationary within a common visceral artery, and adds stability to the outer sheath 204, as the outer sheath 204 is advanced through the introducer sheath 202 to a treatment area in the vasculature. The outer sheath 204 has a body extending from a proximal end 216 to a distal end 210, the body being tubular and including a sheath lumen extending therethrough.

As shown, the assembly 200 may also include a wire guide 208 configured to be percutaneously inserted within the vasculature to guide the outer sheath 204 to the treatment area. The wire guide 208 provides the outer sheath 204 with a path to follow as it is advanced within the body vessel. The size of the wire guide 208 is based on the inside diameter of the outer sheath 204 and the diameter of the target body vessel.

A needle may also be used. The needle may be used for percutaneously introducing the wire guide into the patient's body through an access site. A cutting device 10 may also be used to expand the access site.

When the distal end 210 of the outer sheath 204 is at the desired location in the body vessel, the wire guide 208 is removed and the device 10, having a proximal segment contacting a distal portion 212 of the inner catheter 206, is inserted into the outer sheath 204. The inner catheter 206 is advanced through the outer sheath 204 for deployment of the device 10 through the distal end 210 to treat the body vessel. The catheter 206 extends from a proximal portion 211 to a distal portion 212 and is configured for axial movement relative to the outer sheath 204. In this example, the distal portion 212 is shown adjacent to the device (similar to any of the devices described above). Thus, before deployment, the device 10 is coaxially disposed within the lumen of the outer sheath 204 and removably coupled to the distal portion 212 of the catheter 206, or in the alternative, the device 10 is merely pushed by, but not coupled to, the distal portion 212 of the catheter 206. In this way, the assembly or apparatus may have the inner sheath removably coupled to the filter device 10 at a coupling member.

The outer sheath 204 further has a proximal end 216 and a hub 218 to receive the inner catheter 206 and device 10 to be advanced therethrough. The size of the outer sheath 204 is based on the size of the body vessel in which it percutaneously inserts, and the size of the device 10.

In this embodiment, the device 10 and inner catheter 206 are coaxially advanced through the outer sheath 204, following removal of the wire guide 208, in order to position the device 10 in the body vessel. The device 10 is guided through the outer sheath 204 by the inner catheter 206, preferably from the hub 218, and exits from the distal end 210 of the outer sheath 204 at a location within the vasculature where occlusion is desired. Thus, the device 10 is deployable through the distal end 210 of the outer sheath 204 by means of axial relative movement of the catheter 206. In order to more easily deploy the device 10 into the body vessel, the device 10 may have a lubricious coating, such as silicone or a hydrophilic polymer, e.g. AQ® Hydrophilic Coating as known in the art.

Likewise, in this embodiment the device 10 may also be retrieved by positioning the distal end 210 of the outer sheath 204 adjacent the deployed device in the vasculature. The inner catheter 206 is advanced through the outer sheath 204 until the distal portion 212 protrudes from the distal end 210 of the outer sheath 204. The distal portion 212 is coupled to a proximal end of the device 10, after which the inner catheter 206 is retracted proximally, drawing the device 10 into the outer sheath 204.

If a hook is present in the device 10, such hook may aid in delivery and retrieval. If a hook is not present, the physician may otherwise grasp a proximal portion of the device 10 for delivery and retrieval.

The device 10 has a collapsed state for delivery and an expanded state for filtering once delivered to the appropriate location in the body vessel. In the collapsed state, the device 10 is disposed inside the delivery assembly. The device 10 may be self-expanding to the expanded state upon exiting the delivery assembly for filtering (as shown in FIG. 4B).

The assembly described above is merely one example of an assembly that may be used to deploy the device in a body vessel. Of course, other apparatus, assemblies and systems may be used to deploy any embodiment of the device without falling beyond the scope or spirit of the present invention.

Figure 5:
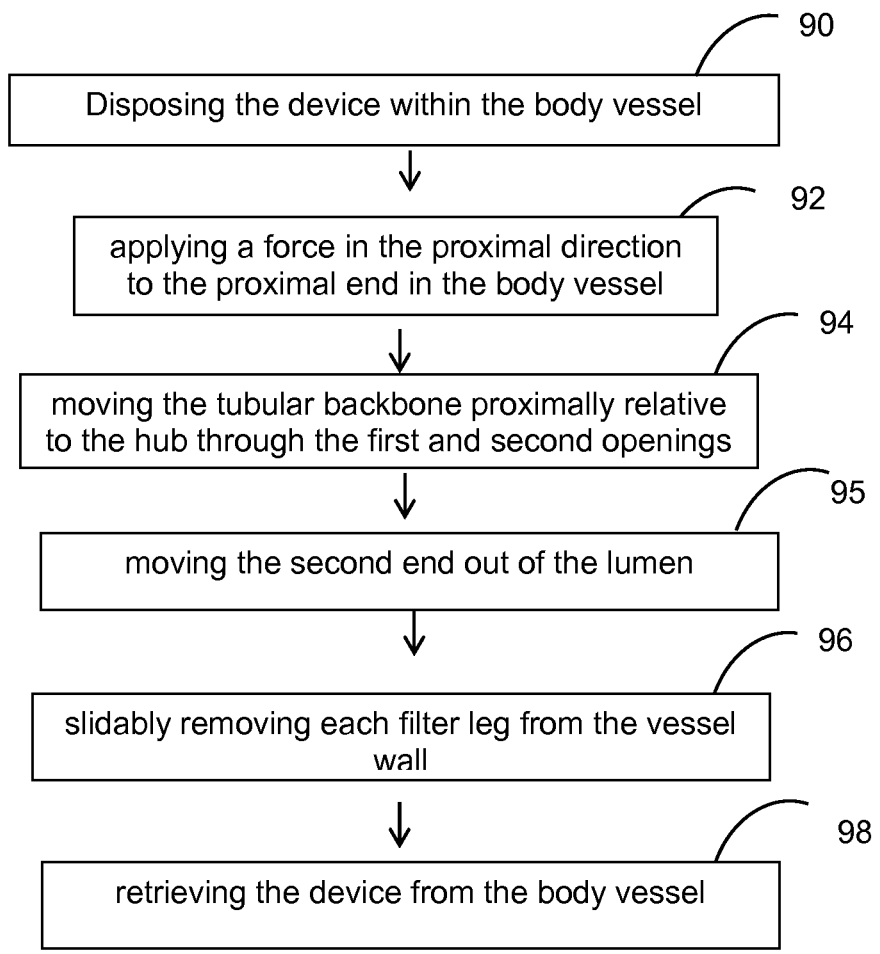
FIG. 5 is a flow diagram of one embodiment of retrieving the device of FIG. 1 from the body vessel in accordance with one embodiment of the present invention.

FIG. 5 depicts a flow diagram of method steps for retrieving the filter device. In step 90, the physician may dispose the device within the body vessel. In step 92, the physician may apply a force in the proximal direction to the proximal end in the body vessel. In step 94, the physician may move the tubular backbone proximally relative to the hub through the first and second openings. In step 95, the physician may move the second end out of the lumen. In step 96, the physician may slidably remove each filter leg from the vessel wall. In step 98, the physician may retrieve the device from the body vessel. The step of disposing the device may comprise centering the device in the body vessel with the first and second arcuate segments.

Figure 6A:
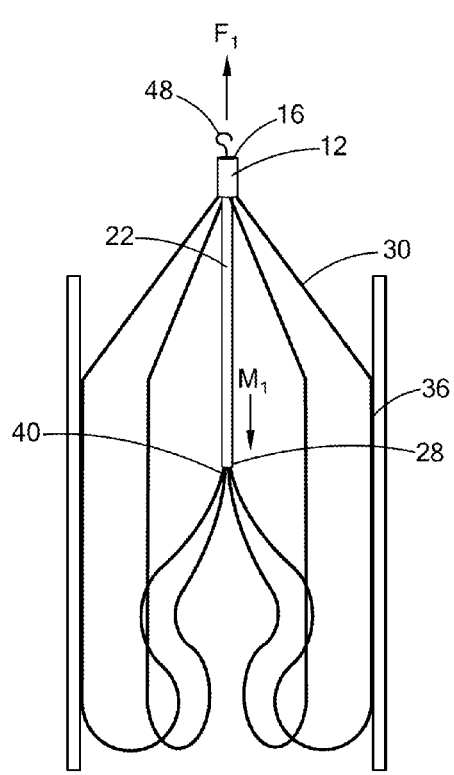
FIGS. 6A-6C depict steps of the method of FIG. 5.
Figure 6B:
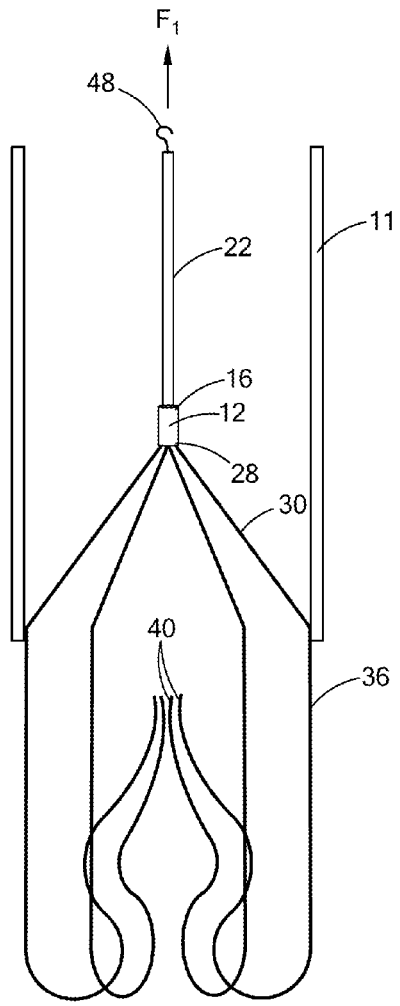
Figure 6C:
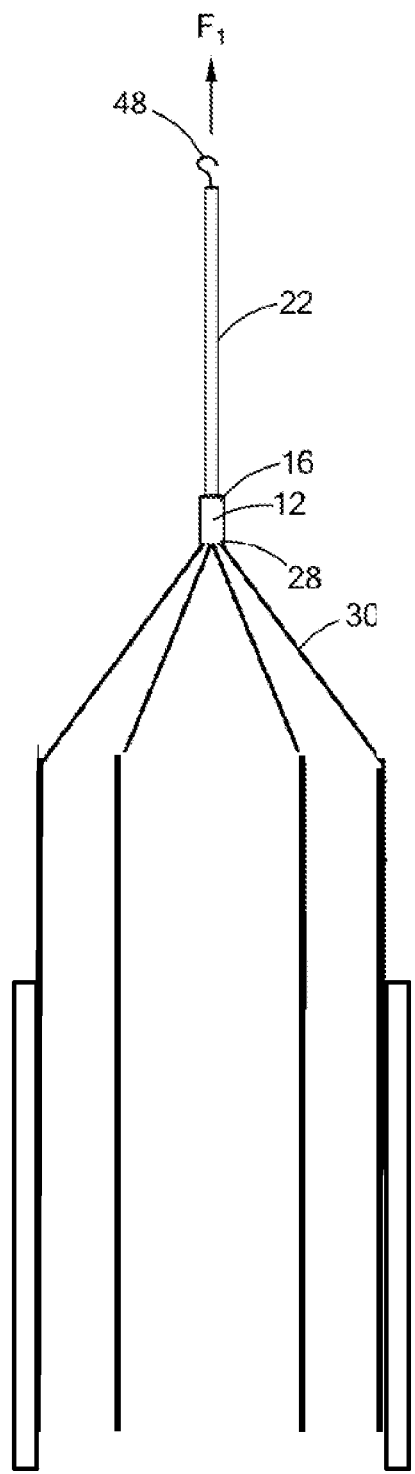

FIGS. 6A-6C illustrate views of the retrieval method of the flow diagram in FIG. 5. In FIG. 6A, the physician may apply a force $F_1$ in the proximal direction to the proximal end of the tubular backbone 22. In the event that the devices has hook 48, this force may be applied to hook 48. In one embodiment, the step of applying comprises sliding the body of the tubular backbone 22 through or relative to the hub 12 between the proximal end and the stop at the distal end 28.

In this embodiment, the force $F_1$ will be great enough to overcome the frictional forces between bore 16 and the tubular backbone 22. However, the force $F_1$ may be low enough to be applied by the physician from a remote location away from the filtering site.

After applying the force $F_1$ the device moves from an expanded position in FIG. 6A to an intermediate, retrieval position in FIG. 6B. In FIG. 6B, the tubular backbone 22 moves or slides proximally relative to the hub 12 so that the hub 12 contacts the distal end 28. The filter legs 30 and the hub 12 may not move due to endothelialization.

The force $F_1$ also moves the second end 40 out of the lumen. Upon the second end 40 exiting the lumen, $F_1$ may overcome the frictional forces between the endothelialized tissue of the vessel wall 11 and each filter leg 30 at the contact portion 36. In this case, force $F_1$ slidably removes each filter leg 30 from the vessel wall 11 through the ingrowth.

In moving through the ingrown, as shown in FIG. 6C, the step of slidably removing includes straightening each filter leg 30 to a substantially straight position. This substantially straight position allows the filter legs to move through any endothelialized tissue, minimalizing or eliminating trauma to the vessel wall. In this manner, each filter leg 30 may be converted from a hair pin or filtering position to a straight position for retrieval.

While the present invention has been described in terms of certain preferred embodiments it will be understood that the invention is not limited to these disclosed embodiments as those having skill in the art may make various modifications without departing from the scope of the following claims.

The invention claimed is:

1. A filter device for filtering in a body vessel having a vessel wall and a longitudinal axis, the device comprising:
    a hub comprising a body with a bore formed therethrough defining a first opening and a second opening;
    a tubular backbone having a proximal end extending to a distal end along the longitudinal axis and a lumen formed therethrough, the tubular backbone being slidably disposed through the hub between the proximal and distal ends; and
    a plurality of filter legs, each filter leg comprising a first portion having a first end attached to the body and extending distally to a contact portion, the contact portion extending to a second portion having a second end removably disposed in the lumen adjacent to the distal end, the second portion having a first arcuate segment connected to the contact portion and extending arcuately to a second arcuate segment, the second arcuate segment extending arcuately to the second end.

2. The device of claim 1 wherein one of the first and second arcuate segments comprises a semicircle.

3. The device of claim 1 wherein the first arcuate segment comprises a first semicircle having a first semicircle end extending from the contact portion to a second semicircle end, the second arcuate segment arcuately extending from the second semicircle end to the second end proximal the second semicircle end.

4. The device of claim 1 having a collapsed state for delivery and an expanded state for treatment.

5. The device of claim 1 wherein one of the first and second arcuate segments extends substantially along a radial direction and the other of the first and second arcuate segments extends substantially along the longitudinal axis.

6. The device of claim 5 wherein the first arcuate segment extends substantially along the radial direction to the second arcuate segment extending substantially along the longitudinal axis.

7. The device of claim 1 wherein the plurality of filter legs is four filter legs, each first end disposed circumferentially around the body about 90 degrees from an adjacent first end.

8. The device of claim 1 wherein the tubular backbone comprises a hook attached to the distal end for delivery and retrieval.

9. The device of claim 1 wherein the tubular backbone comprises a stop at the distal end.

10. The device of claim 1 further comprising a plurality of secondary filter struts, each secondary filter strut having a proximal strut end attached to the body and extending distally to a distal strut end.

11. The device of claim 10 wherein the distal strut end is distal to the distal end and proximal to the first arcuate segment.

12. The device of claim 10 wherein the plurality of secondary filter struts is four secondary filter struts, each proximal strut end being disposed circumferentially around the body about 45 degrees from an adjacent first end.

13. The device of claim 10 wherein the plurality of secondary filter struts is eight secondary filter struts, each proximal strut end being disposed circumferentially around the body about 30 degrees from an adjacent first end and about 30 degrees from an adjacent proximal strut end.

14. The device of claim 1 wherein the contact portion is adapted for contacting the vessel wall.

15. A filter apparatus for filtering in a body vessel having a vessel wall and a longitudinal axis, the apparatus comprising:
    an inner sheath;
    a coupling member; and
    a filter device removably coupled to the inner sheath by way of the coupling member, the filter device comprising:
        a hub comprising a body with a bore formed therethrough defining a first opening and a second opening;
        a tubular backbone having a proximal end extending to a distal end along the longitudinal axis and a lumen formed therethrough, the tubular backbone being slidably disposed through the hub between the proximal and distal ends; and
        a plurality of filter legs, each filter leg comprising a first portion having a first end attached to the body and extending distally to a contact portion, the contact portion extending to a second portion having a second end removably disposed in the lumen adjacent to the distal end, the second portion having a first arcuate segment connected to the contact portion and extending arcuately to a second arcuate segment, the second arcuate segment extending arcuately to the second end.

16. A method of filtering in a body vessel having a vessel wall and a longitudinal axis, the method comprising:
    disposing a filter device in the body vessel, the device comprising:
        a hub comprising a body with a bore formed therethrough defining a first opening and a second opening;
        a tubular backbone having a proximal end extending to a distal end along the longitudinal axis and a lumen formed therethrough, the tubular backbone being slidably disposed through the hub between the proximal and distal ends; and
        a plurality of filter legs, each filter leg comprising a first portion having a first end attached to the body and extending distally to a contact portion, the contact portion extending to a second portion having a second end removably disposed in the lumen adjacent to the distal end, the second portion having a first arcuate segment connected to the contact portion and extending arcuately to a second arcuate segment, the second arcuate segment extending arcuately to the second end;
    applying a force in a proximal direction to the proximal end in the body vessel;
    moving the tubular backbone proximally relative to the hub through the first and second openings;
    moving the second end out of the lumen; and
    slidably removing each filter leg from the vessel wall.

17. The method of claim 16 wherein the step of disposing the filter device comprises centering the device in the body vessel with the first and second arcuate segments.

18. The method of claim 16 wherein the step of moving the tubular backbone comprises sliding the tubular backbone through the body between the proximal end and a stop at the distal end.

19. The method of claim 16 wherein the step of slidably removing each filter leg comprises straightening each filter leg.

20. The method of claim 19 wherein the step of straightening each filter leg comprises straightening each filter leg to a substantially straight position.

* * * * *